US011744609B2

(12) United States Patent
Saterbak et al.

(10) Patent No.: US 11,744,609 B2
(45) Date of Patent: Sep. 5, 2023

(54) HIGH POWER ATHERECTOMY WITH MULTIPLE SAFETY LIMITS

(71) Applicant: BOSTON SCIENTIFIC SCIMED, INC., Maple Grove, MN (US)

(72) Inventors: Matthew Saterbak, Big Lake, MN (US); Corydon Carlson, Stillwater, MN (US); Andrew David Bicek, Elk River, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 227 days.

(21) Appl. No.: 17/174,996

(22) Filed: Feb. 12, 2021

(65) Prior Publication Data

US 2021/0251653 A1 Aug. 19, 2021

Related U.S. Application Data

(60) Provisional application No. 62/978,600, filed on Feb. 19, 2020.

(51) Int. Cl.
*A61B 17/3207* (2006.01)
*G16H 40/60* (2018.01)
(Continued)

(52) U.S. Cl.
CPC ..... *A61B 17/320758* (2013.01); *G16H 40/60* (2018.01); *A61B 2017/320032* (2013.01); *A61B 2090/031* (2016.02); *A61B 2090/0807* (2016.02)

(58) Field of Classification Search
CPC .......... A61B 17/3207; A61B 17/32037; A61B 17/320758; A61B 2090/031
See application file for complete search history.

(56) References Cited

U.S. PATENT DOCUMENTS 5,478,344 A 12/1995 Stone
5,584,861 A 12/1996 Swain et al.
(Continued)

FOREIGN PATENT DOCUMENTS

CA 2682488 A1 10/2008
DE 202005022017 U1 5/2012
(Continued)

OTHER PUBLICATIONS

International Search Report and Written Opinion dated Aug. 20, 2019 for International Application No. PCT/US2019/033748.
(Continued)

*Primary Examiner* — Tuan V Nguyen
(74) *Attorney, Agent, or Firm* — Seager, Tufte & Wickhem LLP

(57) ABSTRACT

An atherectomy system includes an electric drive mechanism that is adapted to rotatably actuate an atherectomy burr and a controller that is adapted to regulate operation of the electric drive mechanism. The controller regulates operation of the electric drive mechanism in accordance with a power input limit value that limits how much power can be put into an atherectomy burr and an energy input limit value that limits how much energy can be put into the atherectomy burr. The controller may also regulate operation of the electric drive mechanism in accordance with a dynamic torque limit.

18 Claims, 7 Drawing Sheets

(51) Int. Cl.
*A61B 90/00* (2016.01)
*A61B 17/32* (2006.01)

(56) References Cited

U.S. PATENT DOCUMENTS

| | | | |
|---|---|---|---|
| 6,086,608 A | 7/2000 | Ek et al. |
| 6,200,329 B1 | 3/2001 | Fung et al. |
| 6,494,888 B1 | 12/2002 | Laufer et al. |
| 6,506,196 B1 | 1/2003 | Laufer |
| 6,554,845 B1 | 4/2003 | Fleenor et al. |
| 6,569,085 B2 | 5/2003 | Kortenbach et al. |
| 6,626,917 B1 | 9/2003 | Craig |
| 6,663,639 B1 | 12/2003 | Laufer et al. |
| 6,719,763 B2 | 4/2004 | Chung et al. |
| 6,740,030 B2 | 5/2004 | Martone et al. |
| 6,746,457 B2 | 6/2004 | Dana et al. |
| 6,755,843 B2 | 6/2004 | Chung et al. |
| 6,773,441 B1 | 8/2004 | Laufer et al. |
| 6,808,491 B2 | 10/2004 | Kortenbach et al. |
| 6,821,285 B2 | 11/2004 | Laufer et al. |
| 6,835,200 B2 | 12/2004 | Laufer et al. |
| 6,908,427 B2 | 6/2005 | Fleener et al. |
| 6,997,931 B2 | 2/2006 | Sauer et al. |
| 7,056,284 B2 | 6/2006 | Martone et al. |
| 7,063,710 B2 | 6/2006 | Takamoto et al. |
| 7,063,715 B2 | 6/2006 | Onuki et al. |
| 7,094,246 B2 | 8/2006 | Anderson et al. |
| 7,144,401 B2 | 12/2006 | Yamamoto et al. |
| 7,147,646 B2 | 12/2006 | Dana et al. |
| 7,153,314 B2 | 12/2006 | Laufer et al. |
| 7,220,266 B2 | 5/2007 | Gambale |
| 7,232,445 B2 | 6/2007 | Kortenbach et al. |
| 7,235,086 B2 | 6/2007 | Sauer et al. |
| 7,326,221 B2 | 2/2008 | Sakamoto et al. |
| 7,344,545 B2 | 3/2008 | Takemoto et al. |
| 7,347,863 B2 | 3/2008 | Rothe et al. |
| 7,361,180 B2 | 4/2008 | Saadat et al. |
| 7,530,985 B2 | 5/2009 | Takemoto et al. |
| 7,601,161 B1 | 10/2009 | Nobles et al. |
| 7,618,425 B2 | 11/2009 | Yamamoto et al. |
| 7,713,277 B2 | 5/2010 | Laufer et al. |
| 7,722,633 B2 | 5/2010 | Laufer et al. |
| 7,727,246 B2 | 6/2010 | Sixto, Jr. et al. |
| 7,736,373 B2 | 6/2010 | Laufer et al. |
| 7,776,057 B2 | 8/2010 | Laufer et al. |
| 7,776,066 B2 | 8/2010 | Onuki et al. |
| 7,842,051 B2 | 11/2010 | Dana et al. |
| 7,846,180 B2 | 12/2010 | Cerier |
| 7,857,823 B2 | 12/2010 | Laufer et al. |
| 7,896,893 B2 | 3/2011 | Laufer et al. |
| 7,918,867 B2 | 4/2011 | Dana et al. |
| 7,951,157 B2 | 5/2011 | Gambale |
| 7,992,571 B2 | 8/2011 | Gross et al. |
| 7,993,368 B2 | 8/2011 | Gambale et al. |
| 8,016,840 B2 | 9/2011 | Takemoto et al. |
| 8,021,376 B2 | 9/2011 | Takemoto et al. |
| 3,062,314 A1 | 11/2011 | Sixto, Jr. et al. |
| 8,057,494 B2 | 11/2011 | Laufer et al. |
| 8,066,721 B2 | 11/2011 | Kortenbach et al. |
| 8,105,355 B2 | 1/2012 | Page et al. |
| 8,211,123 B2 | 7/2012 | Gross et al. |
| 8,216,253 B2 | 7/2012 | Saadat et al. |
| 8,226,667 B2 | 7/2012 | Viola et al. |
| 8,277,468 B2 | 10/2012 | Laufer et al. |
| 8,287,554 B2 | 10/2012 | Cerier et al. |
| 8,287,556 B2 | 10/2012 | Gilkey et al. |
| 8,308,765 B2 | 11/2012 | Saadat et al. |
| 8,313,496 B2 | 11/2012 | Sauer et al. |
| 8,361,089 B2 | 1/2013 | Chu |
| 8,388,632 B2 | 3/2013 | Gambale |
| 8,425,555 B2 | 4/2013 | Page et al. |
| 8,454,631 B2 | 6/2013 | Viola et al. |
| 8,480,691 B2 | 7/2013 | Dana et al. |
| 8,540,735 B2 | 9/2013 | Mitelberg et al. |
| 8,551,120 B2 | 10/2013 | Gambale |
| 8,585,720 B2 | 11/2013 | Gross et al. |
| 8,632,553 B2 | 1/2014 | Sakamoto et al. |
| 8,679,136 B2 | 3/2014 | Mitelberg |
| 8,709,022 B2 | 4/2014 | Stone et al. |
| 8,764,771 B2 | 7/2014 | Chu |
| 8,882,785 B2 | 11/2014 | DiCesare et al. |
| 8,926,634 B2 | 1/2015 | Rothe et al. |
| 8,992,570 B2 | 3/2015 | Gambale et al. |
| 9,011,466 B2 | 4/2015 | Adams et al. |
| 9,050,126 B2 † | 6/2015 | Rivers |
| 9,089,325 B2 | 7/2015 | Mitelberg et al. |
| 9,125,646 B2 | 9/2015 | Woodard, Jr. et al. |
| 9,198,562 B2 | 12/2015 | Mitelberg et al. |
| 9,320,515 B2 | 4/2016 | Dana et al. |
| 9,486,126 B2 | 11/2016 | West et al. |
| 9,504,465 B2 | 11/2016 | Chu |
| 9,510,817 B2 | 11/2016 | Saadat et al. |
| 9,549,728 B2 | 1/2017 | Chu |
| 9,750,494 B2 | 9/2017 | Gross et al. |
| 9,788,831 B2 | 10/2017 | Mitelberg |
| 9,844,366 B2 | 12/2017 | Woodard, Jr. et al. |
| 9,867,610 B2 | 1/2018 | Mitelberg et al. |
| 10,045,871 B2 | 8/2018 | Saadat et al. |
| 10,052,122 B2 | 8/2018 | Higgins et al. |
| 10,143,463 B2 | 12/2018 | Dana et al. |
| 10,194,902 B2 | 2/2019 | Nobles et al. |
| 10,335,142 B2 | 7/2019 | Raybin et al. |
| 2002/0058956 A1* | 5/2002 | Honeycutt ..... A61B 17/320758 606/159 |
| 2002/0107530 A1 | 8/2002 | Sauer et al. |
| 2003/0204205 A1 | 10/2003 | Sauer et al. |
| 2004/0002699 A1 | 1/2004 | Ryan et al. |
| 2004/0138706 A1 | 7/2004 | Abrams et al. |
| 2004/0220519 A1 † | 11/2004 | Wulfman |
| 2005/0033319 A1 | 2/2005 | Gambale et al. |
| 2005/0250985 A1 | 11/2005 | Saadat et al. |
| 2006/0282094 A1 | 12/2006 | Stokes et al. |
| 2007/0270908 A1 | 11/2007 | Stokes et al. |
| 2008/0086148 A1 | 4/2008 | Baker et al. |
| 2009/0177031 A1 | 7/2009 | Surti et al. |
| 2010/0137681 A1 | 6/2010 | Ewers et al. |
| 2010/0198006 A1 | 8/2010 | Greenburg et al. |
| 2012/0158023 A1 | 6/2012 | Miltelberg et al. |
| 2012/0271327 A1 | 10/2012 | West et al. |
| 2013/0096581 A1 | 4/2013 | Gilkey et al. |
| 2013/0304093 A1 | 11/2013 | Serina et al. |
| 2014/0121457 A1 | 5/2014 | Mort et al. |
| 2014/0128668 A1 | 5/2014 | Cox et al. |
| 2015/0126983 A1 | 5/2015 | Alvarado et al. |
| 2016/0045197 A1 | 2/2016 | Mitelberg et al. |
| 2017/0042534 A1 | 2/2017 | Nobles et al. |
| 2017/0086817 A1 | 3/2017 | Mitelberg |
| 2017/0086818 A1 | 3/2017 | Mitelberg |
| 2017/0119371 A1 | 5/2017 | Mims et al. |
| 2017/0319197 A1 | 11/2017 | Gross et al. |
| 2018/0042602 A1 | 2/2018 | Mitelberg et al. |
| 2018/0042603 A1 | 2/2018 | Mitelberg et al. |
| 2018/0153381 A1 | 6/2018 | Wei et al. |
| 2018/0221009 A1 | 8/2018 | Mitelberg et al. |
| 2018/0235604 A1 | 8/2018 | Comee et al. |
| 2018/0344501 A1 | 12/2018 | Saadat et al. |
| 2019/0175211 A1 | 6/2019 | Carlson et al. |
| 2019/0262032 A1 | 8/2019 | Carlson et al. |
| 2019/0262034 A1 | 8/2019 | Spangler et al. |

FOREIGN PATENT DOCUMENTS

| | | |
|---|---|---|
| EP | 1520509 A1 | 4/2005 |
| EP | 2108304 A2 | 10/2009 |
| WO | 0189393 A1 | 11/2001 |
| WO | 2008016592 A2 | 2/2008 |
| WO | 2008045376 A2 | 4/2008 |
| WO | 2008098124 A1 | 8/2008 |
| WO | 2010036227 A1 | 4/2010 |
| WO | 2011106053 A1 | 9/2011 |
| WO | 2016200811 A1 | 12/2016 |

(56) References Cited

FOREIGN PATENT DOCUMENTS

WO          2017087856 A1     5/2017
WO          2018156603 A1     8/2018

OTHER PUBLICATIONS

International Search Report and Written Opinion dated Oct. 1, 2019 for International Application No. PCT/US2019/038006.
Invitation to Pay Additional Fees dated Sep. 26, 2019 for International Application No. PCT/US2019/037995.
International Search Report and Written Opinion dated Dec. 6, 2019 for International Application No. PCT/US2019/037995.
International Search Report and Written Opinion dated Nov. 18, 2019 for International Application No. PCT/US2019/049774.
International Search Report and Written Opinion dated Sep. 20, 2019 for International Application No. PCT/US2019/039312.
International Search Report and Written Opinion dated Jun. 4, 2021 for International Application No. PCT/US2021/017939.

\* cited by examiner
† cited by third party

HIGH POWER ATHERECTOMY WITH MULTIPLE SAFETY LIMITS

CROSS-REFERENCE TO RELATED APPLICATIONS

This application claims the benefit of priority under 35 U.S.C. § 119 to U.S. Provisional Application Ser. No. 62/978,600, filed Feb. 19, 2020, the entirety of which is incorporated herein by reference.

TECHNICAL FIELD

The present disclosure pertains to medical devices, and methods for manufacturing and using medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

Many patients suffer from occluded arteries and other blood vessels which restrict blood flow. Occlusions can be partial occlusions that reduce blood flow through the occluded portion of a blood vessel or total occlusions (e.g., chronic total occlusions) that substantially block blood flow through the occluded blood vessel. In some cases, a stent may be placed in the area of a treated occlusion. However, restenosis may occur in the stent, further occluding the vessel and restricting blood flow. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. A need remains for alternative atherectomy devices to facilitate crossing an occlusion.

SUMMARY

This disclosure provides design, material, manufacturing method, and use alternatives for medical devices. As an example, an atherectomy system includes an electric drive mechanism that is adapted to rotatably actuate an atherectomy burr and a controller that is adapted to regulate operation of the electric drive mechanism, the controller regulating operation of the electric drive mechanism in accordance with a power input limit value that limits how much power can be exerted at the atherectomy burr and an energy input limit value that limits how much energy can be exerted at the atherectomy burr.

Alternatively or additionally, the electric drive mechanism may include a drive cable that is adapted to be coupled with an atherectomy burr and an electric drive motor that is adapted to rotate the drive cable.

Alternatively or additionally, the atherectomy system may further include an atherectomy burr that is rotatably secured to the drive cable.

Alternatively or additionally, the controller may be further adapted to regulate operation of the electric drive mechanism in accordance with a dynamic torque limit value.

Alternatively or additionally, the dynamic torque limit value may vary in accordance with operating speed of the electric drive mechanism.

Alternatively or additionally, the controller may be further adapted to provide feedback to an operator of the atherectomy system when either the power input limit value and/or the energy input limit value are exceed during operation of the atherectomy system.

Alternatively or additionally, the feedback may include a temporary reduction in an operating speed of the electric drive mechanism.

Alternatively or additionally, the controller may include a speed reference block that includes the power input limit value and the energy input limit value and is configured to output a reference signal, a control block that is adapted to receive the reference signal from the speed reference block and generate a control effort signal and a drive motor circuit block that is adapted to receive the control effort signal from the control block and regulate operation of the electric drive mechanism accordingly.

Alternatively or additionally, the drive motor circuit block may include the dynamic torque limit value and may regulate operation of the electric drive mechanism accordingly.

Alternatively or additionally, the dynamic torque limit values may include a current limit value.

Alternatively or additionally, the control block may include a Proportional Integral Derivative (PID) controller.

As another example, an atherectomy system includes an electric drive motor that is operably coupled to a drive cable, an atherectomy burr that is operably coupled to the drive cable and a control system that is operably coupled to the drive motor. The control system includes a speed reference block that includes a power input limit value and an energy input limit value and is configured to output a reference signal, a control block that is adapted to receive the reference signal from the speed reference block and generate a control effort signal and a drive motor circuit block that is adapted to receive the control effort signal from the control block and regulate operation of the electric drive mechanism accordingly.

Alternatively or additionally, the control block may further include a state estimation block that receives a position signal from the electric drive motor and outputs a motor speed signal that is summed with the reference signal from the speed reference block.

Alternatively or additionally, the electric drive motor may include a brushless DC electric motor.

Alternatively or additionally, the drive motor circuit block may further include a dynamic torque limit value and regulates operation of the electric drive mechanism accordingly.

Alternatively or additionally, the dynamic torque limit values may include a current limit value.

Alternatively or additionally, the control block may include a Proportional Integral Derivative (PID) controller.

As another example, an atherectomy system includes an electric drive motor that is operably coupled to a drive cable, an atherectomy burr that is operably coupled to the drive cable and a control system that is operably coupled to the drive motor. The control system includes a speed reference block that includes a power input limit value and an energy input limit value and is configured to output a reference signal that is limited by at least one of the power input limit value and the energy input limit value, a control block that is adapted to receive the reference signal from the speed reference block and generate a control effort signal, and a drive motor circuit block that is adapted to receive the control effort signal from the control block and includes a dynamic torque limit and regulates operation of the electric drive motor in accordance with the control effort signal and the dynamic torque limit.

Alternatively or additionally, the control system may be further adapted to provide feedback to an operator of the atherectomy system when any of the power input limit value, the energy input limit value or the dynamic torque limit are approached or exceeded during operation of the atherectomy system.

Alternatively or additionally, the feedback may include a discernible reduction in an operating speed of the electric drive mechanism.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
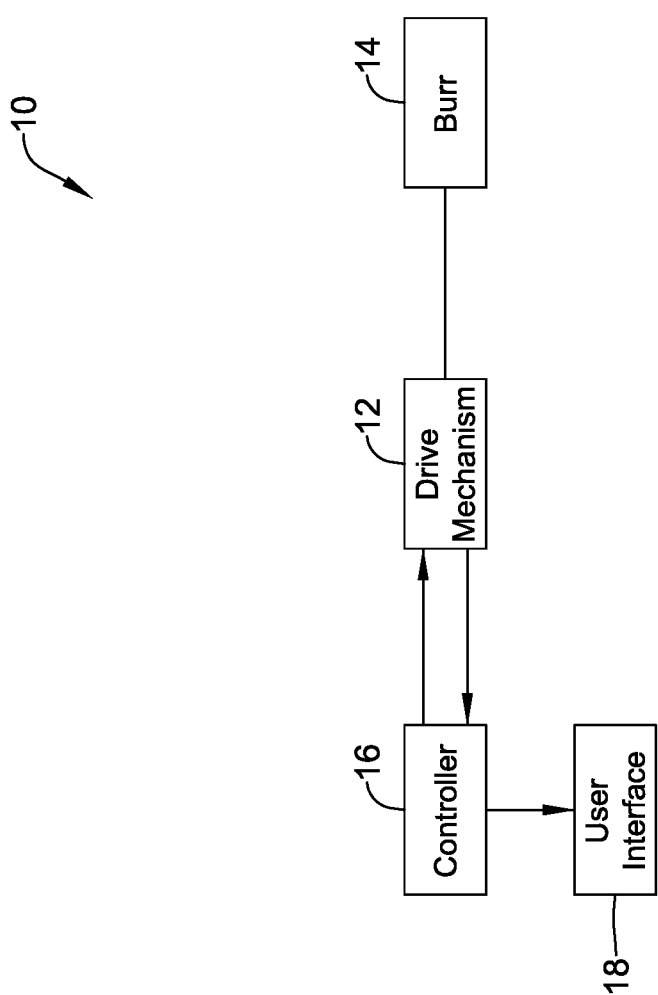
FIG. 1 is a schematic block diagram of an example atherectomy system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Many patients suffer from occluded arteries, other blood vessels, and/or occluded ducts or other body lumens which may restrict bodily fluid (e.g. blood, bile, etc.) flow. Occlusions can be partial occlusions that reduce blood flow through the occluded portion of a blood vessel or total occlusions (e.g., chronic total occlusions) that substantially block blood flow through the occluded blood vessel. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. Ideally, the cutting element excises the occlusion without damaging the surrounding vessel wall and/or a previously implanted stent where restenosis has occurred. However, in some instances the cutting element may be manipulated and/or advanced such that it contacts the vessel wall and/or the stent. Therefore, it may be desirable to utilize materials and/or design an atherectomy device that can excise an occlusion without damaging the surrounding vessel and/or a previously implanted stent where restenosis has occurred. Additionally, it may be desirable that a cutting element be useful in removing hard occlusive material, such as calcified material, as well as softer occlusive material. The methods and systems disclosed herein may be designed to overcome at least some of the limitations of previous atherectomy devices while effectively excising occlusive material. For example, some of the devices and methods disclosed herein may include cutting elements with unique cutting surface geometries and/or designs.

FIG. 1 is a schematic block diagram of an example atherectomy system 10 that includes a drive mechanism 12 that is adapted to rotatably actuate an atherectomy burr 14. While the example atherectomy system 10 is described herein as an electrically actuated atherectomy system, it will be appreciated that in some cases the atherectomy system 10 may instead be pneumatically actuated in which compressed air or another compressed fluid is used to drive a turbine that actuates the atherectomy burr 14. Illustrative but non-limiting examples of pneumatically actuated atherectomy systems include the Jetstream™ atherectomy system and the ROTABLATOR™ atherectomy systems available commercially from Boston Scientific Corporation.

The atherectomy system 10 includes a controller 16 that is adapted to regulate operation of the drive mechanism 12. In some cases, the atherectomy system 10 may include a user interface 18 that may be operably coupled to the controller 16 such that the controller 16 is able to display information regarding the performance of the drive mechanism 12. This information may, for example, include one or more of an instantaneous speed of the drive mechanism 12, an instantaneous torque being experienced by the atherectomy burr 14, and the like. In some instances, the atherectomy system 10 may not include the user interface 18. In some cases, the atherectomy burr 14 may also be referred to as being or including a cutting head or a cutting member, and these terms may be used interchangeably.

Figure 2:
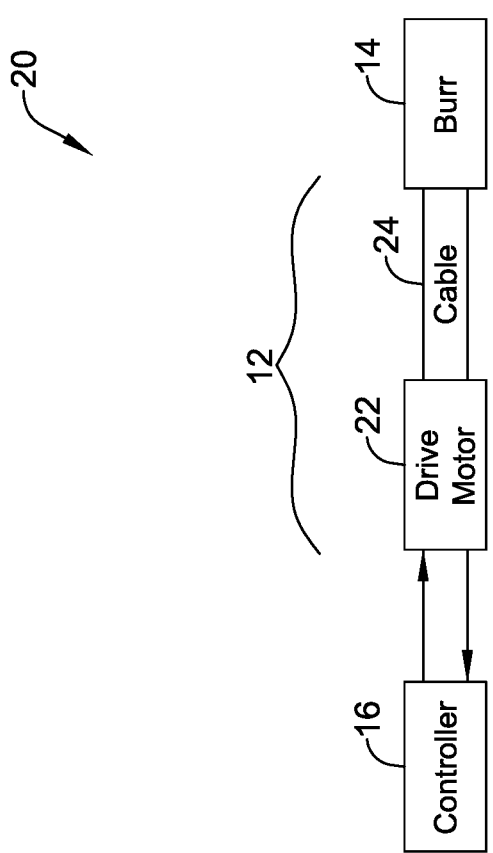
FIG. 2 is a schematic block diagram of an example atherectomy system.

FIG. 2 is a schematic block diagram of an example atherectomy system 20 in which the drive mechanism 12 may include a drive motor 22 and a drive cable 24 that is operably coupled with the drive motor 22 as well as the atherectomy burr 14. In some cases, features of the atherectomy system 20 may be combined with features of the atherectomy system 10. In some cases, the atherectomy system 20 may also include a handle (not shown). In some cases, the drive motor 22 may be sized, relative to the weight and other dimensions of the atherectomy system 20, to be capable of accelerating the atherectomy burr to full speed in less than 3 seconds, or in some cases in less than 2 seconds. As an example, the motor 22 may be rated for at least 60 watts. In a particular example, the motor 22 may be rated for about 80 watts. These are just examples.

Figure 3:
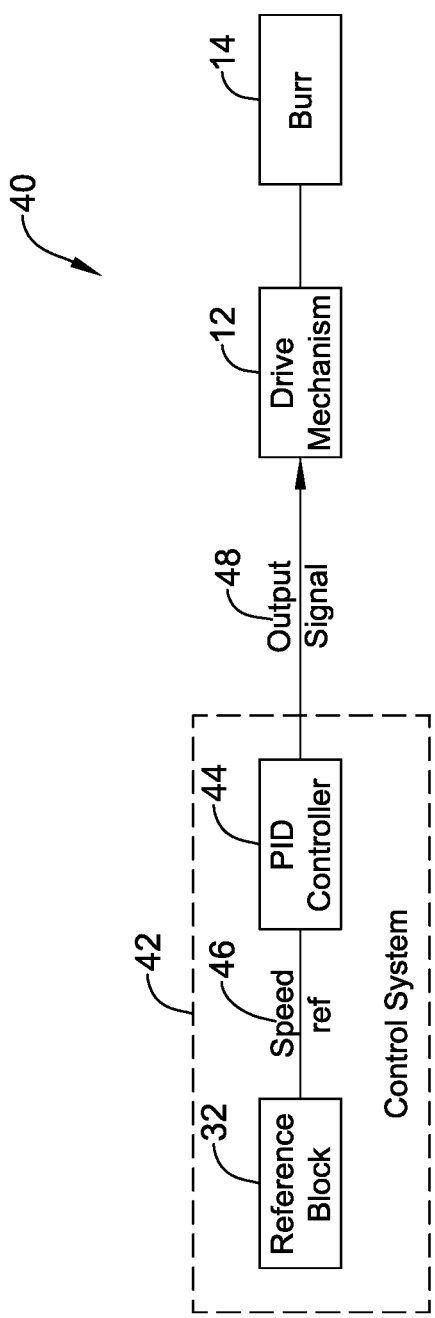
FIG. 3 is a schematic block diagram of an example atherectomy system.

FIG. 3 is a schematic block diagram of an example atherectomy system 40 that includes a control system 42 that is adapted to regulate operation of the drive mechanism 12 in order to rotatably actuate the atherectomy burr 14. In some cases, features of the atherectomy system 40 may be combined with one or more of the atherectomy system 10 and the atherectomy system 20. The control system 42 may include a reference block 32 as well as a Proportional Integral Derivative (PID) controller 44 that is operably coupled to the reference block 32. In some cases, the reference block 32 may determine a speed reference 46 that is selectable between a nominal value, a negative value and zero. In some instances, the PID controller 44 may be further adapted to add an offset value to the speed reference 46 received from the reference block 32, thereby outputting an Output Signal 48, although in some cases, the reference block 32 may add the offset value.

Figure 4:
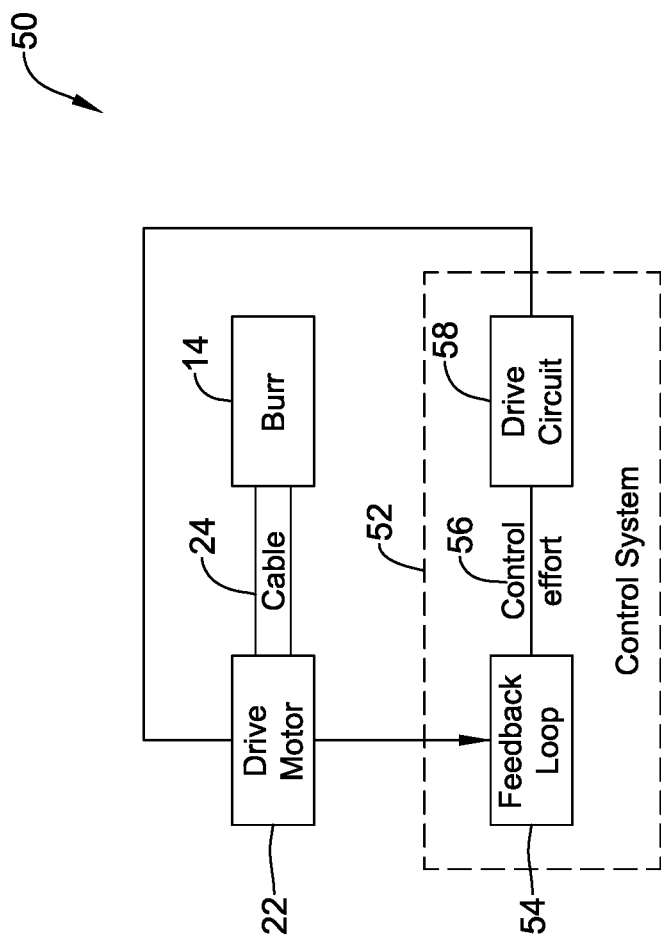
FIG. 4 is a schematic block diagram of an example atherectomy system.

FIG. 4 is a schematic block diagram of an example atherectomy system 50 that includes a control system 52 that is adapted to regulate operation of the drive motor 22 in order to rotatably actuate the atherectomy burr 14. In some cases, features of the atherectomy system 50 may be combined with one or more of the atherectomy system 10, the atherectomy system 20 or the atherectomy system 40. The control system 52 is operably coupled to the drive motor 22 and includes a feedback loop 54 that is adapted to monitor performance of the drive motor 22 and to output a control effort signal 56. A drive circuit 58 is adapted to receive the control effort signal 56 and to regulate operation of the drive motor 22 in accordance with the control effort signal 56.

In some cases, the feedback loop 54 may include a reference block for determining a speed reference and a Proportional Integral Derivative (PID) controller that is operably coupled to the reference block for receiving the speed reference, the PID controller adapted to utilize the speed reference, a Proportional (P) gain value, an Integral (I) gain value and a Derivative (D) gain value in determining the control effort signal. In some cases, the feedback loop 54 may be adapted to add an offset value to a reference signal provided to the reference loop 54 in order to accurately hold speed of the drive motor 22 during a no-load situation. In some instances, for example if the atherectomy burr 14 becomes stuck, the control system 52 may be further adapted to increase the torque provided by the drive motor 22 until a torque threshold is reached for a brief period of time, and to subsequently direct the drive motor 22 to reverse at a slow speed in order to unwind energy in the drive mechanism.

Figure 5:
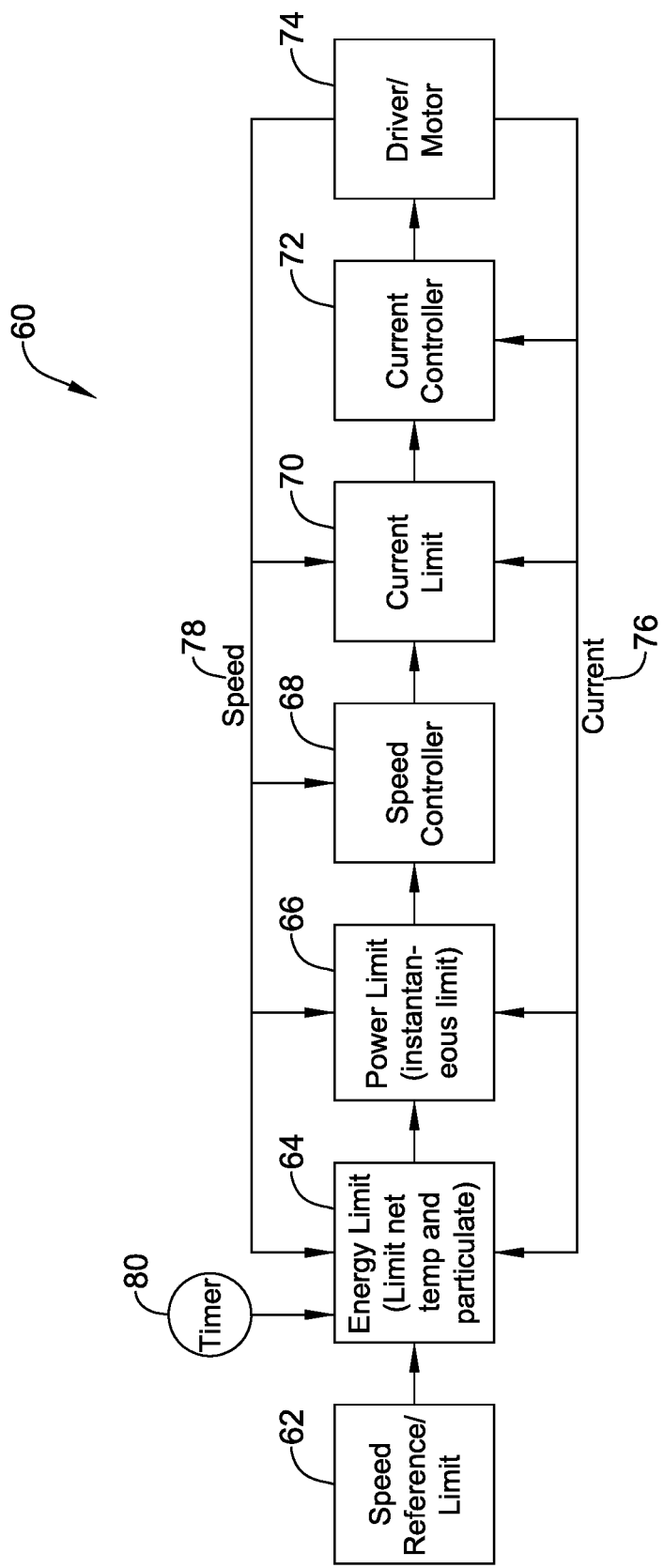
FIG. 5 is a schematic block diagram of an example atherectomy system.

FIG. 5 is a schematic block diagram showing an illustrative control algorithm 60 that may, for example, be implemented within any of the controller 16 (FIGS. 1 and 2), the control system 42 (FIG. 3) or the control system 52 (FIG. 4). In some cases, for example, the illustrative control algorithm 60 provides an atherectomy system such as the atherectomy system 10, 20, 40, 50 with additional safeguards to help protect the patient. It will be appreciated that in performing rotational atherectomy, there are limits as to how much power and energy may be put into a patient. Putting in too much power, for example, while increasing ablation speeds, can also result in vessel trauma. Putting in too much energy can result in excessive steady state temperature increases in the patient near the atherectomy burr. It will be appreciated that power and energy are related, as power is defined as energy per time. The illustrative control algorithm 60 may also be considered as providing dynamic torque limits. In some cases, the amount of torque that can be applied can vary with rotational speed. Additional torque may be needed, for example, when initially starting to rotate the atherectomy burr as it is necessary to overcome the inertia of the drive mechanism (such as the drive mechanism 12). The illustrative control algorithm 60 may be viewed as having a number of blocks. A speed reference block 62 provides a signal indicating a speed reference. The speed reference may have a speed limit that is stored within the speed reference block 62 and that may provide a throttling effect on the outputted speed signal.

An energy limit block 64 stores an energy input limit value that limits how much energy can be exerted at the atherectomy burr 14. In some cases, the energy input limit value may be considered as being self-resetting in order to account for how fast heat can dissipate. The energy limit block 64 may account for system inefficiency by estimating energy exerted at the atherectomy burr as opposed to energy lost to the ambient environment outside of the patient.

A power limit block 66 stores a power input limit value that limits how much time-averaged power can be exerted at the atherectomy burr 14. The power limit block 66 may, in some cases, reference a known limit to safe average power and only outputs a speed-reducing signal when the known limit is approached or exceeded. The power limit block 66 may account for system inefficiency by estimating power put into the atherectomy burr 14 as opposed to power lost to the ambient environment outside of the patient.

A speed controller 68 receives inputs from each of the speed reference block 62, the energy limit block 64 and the power limit block 66 and determines an appropriate speed for operating the drive mechanism. A current limit block 70 receives a signal from the speed controller 68 and includes a current input limit value that limits how much torque may be applied via the atherectomy system. The current limit block 70 provides a signal to a current controller 72, which monitors for excessive current (torque) and outputs a drive signal to a drive motor 74. It will be appreciated that the drive motor 74 represents the drive motor 22 shown in previous FIGS.

The illustrative control algorithm 60 may be considered as being a feedback algorithm. As can be seen, the drive motor 74 outputs a current signal 76 that may be provided to one or more of the energy limit block 64, the power limit block 66, the current limit block 70 and the current controller 72. Similarly, the drive motor 74 outputs a speed signal 78 that is provided to one or more of the energy limit block 64, the power limit block 66, the speed controller 68 and the current limit block 70. A timer 80 provides a timer signal to the energy limit block 64, which allows the control algorithm 60 to calculate power from energy, and vice versa.

Figure 6:
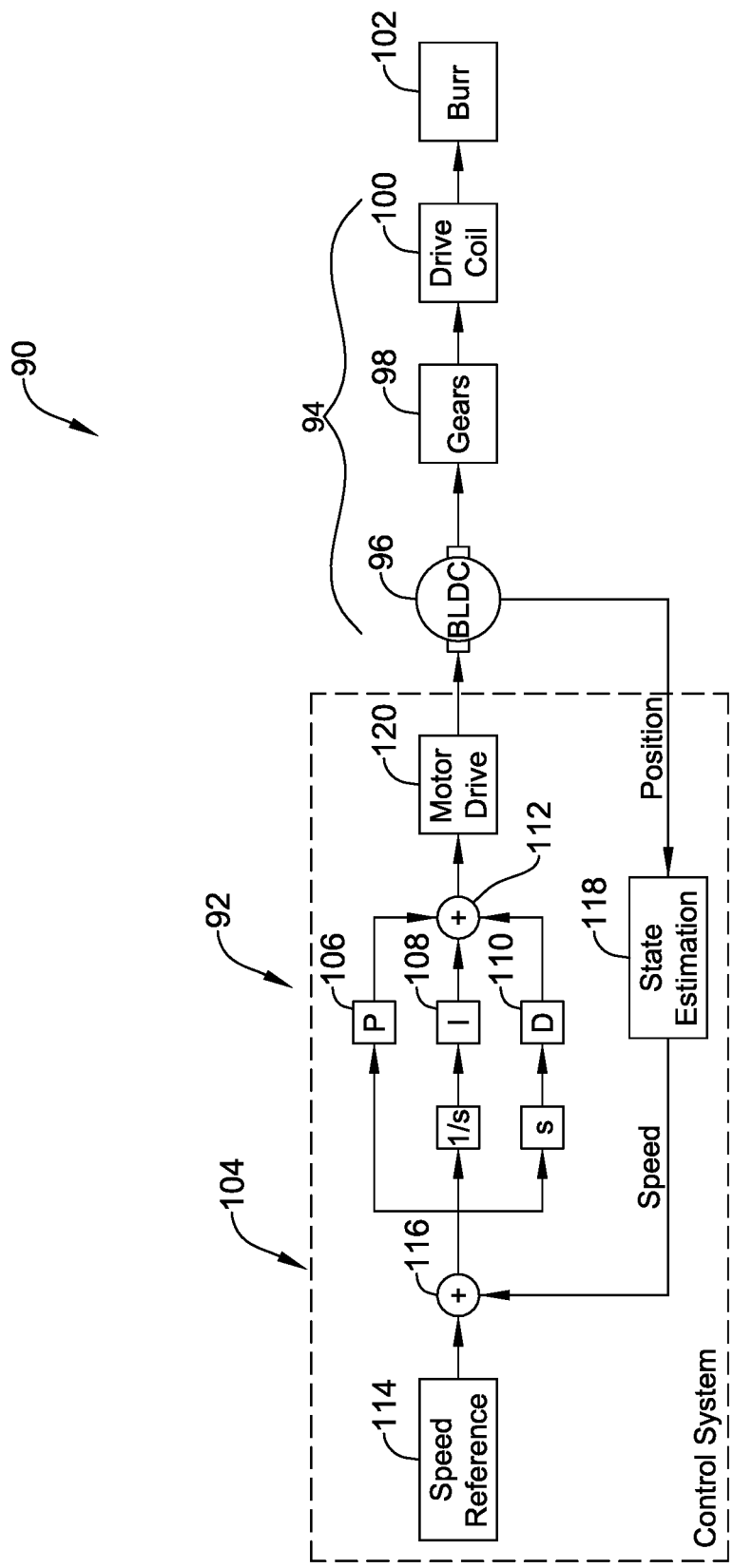
FIG. 6 is a schematic block diagram of an example atherectomy system.

FIG. 6 is a schematic block diagram of an example atherectomy system 90. In some cases, features of the atherectomy system 90 may be combined with one or more of the atherectomy system 10, the atherectomy system 20, the atherectomy system 40 or the atherectomy system 50. The example atherectomy system 90 includes a Control System 92 and a drive mechanism 94. The drive mechanism 94 includes a drive motor 96 which, in some cases as illustrated, may be a brushless DC electric motor. The drive mechanism 94 includes a set of gears 98 that provides a desired gear reduction relative to an output of the drive motor 96. A drive coil 100 represents a drive cable such as the drive cable 24, which is oftentimes modeled and treated as a spring coil due to how the drive cable 24 reacts to rotation. An atherectomy burr 102 is shown coupled with the drive coil 100.

The Control System 92 includes a Proportional Integral Derivative (PID) controller 104 that provides a Proportional (P) term 106, an Integral (I) term 108 and a Derivative (D) term 110 to a Summation Block 112. A Speed Reference Block 114 provides a speed reference value to a Summation Block 116, where the speed reference value is summed with a speed value provided by a State Estimation block 118. The State Estimation block 118 receives a position signal from the drive motor 96. A motor drive block 120 receives a signal from the Summation Block 112 and outputs a drive signal to the drive motor 96.

It will be appreciated that the Control System 92 may be considered as being adapted to provide the functionality described with respect to the control algorithm 60. In some cases, for example, the Speed Reference Block 114 stores or otherwise includes the power input limit value that limits how much time-averaged power can be put into the atherectomy burr 102 and/or the drive coil 100 as well as the energy input limit value that limits how much energy can be put into the atherectomy burr 102 and/or the drive coil 100. In some instances, a moving average may be used that is related to a thermal time constant for the particular tissue of concern. In some cases, the Motor Drive Block 120 may store or otherwise include the dynamic torque limit value. The dynamic torque limit value may be expressed in terms of current, for example.

In some cases, if one or more of the energy input limit value, the power (or time-averaged power input limit value and the dynamic torque limit value approaches or exceeds a predetermined safety limit, the control system 92 may institute a speed reduction that is sufficient to be noticeable to a user of the system. The system is not stopped, just temporarily slowed down. In some cases, this may be stepped, as a first speed reduction may be instituted as one of the safety limits is approached, with perhaps a second speed reduction (greater than the first) may be instituted as one of the safety limits is exceeded.

Figure 7:
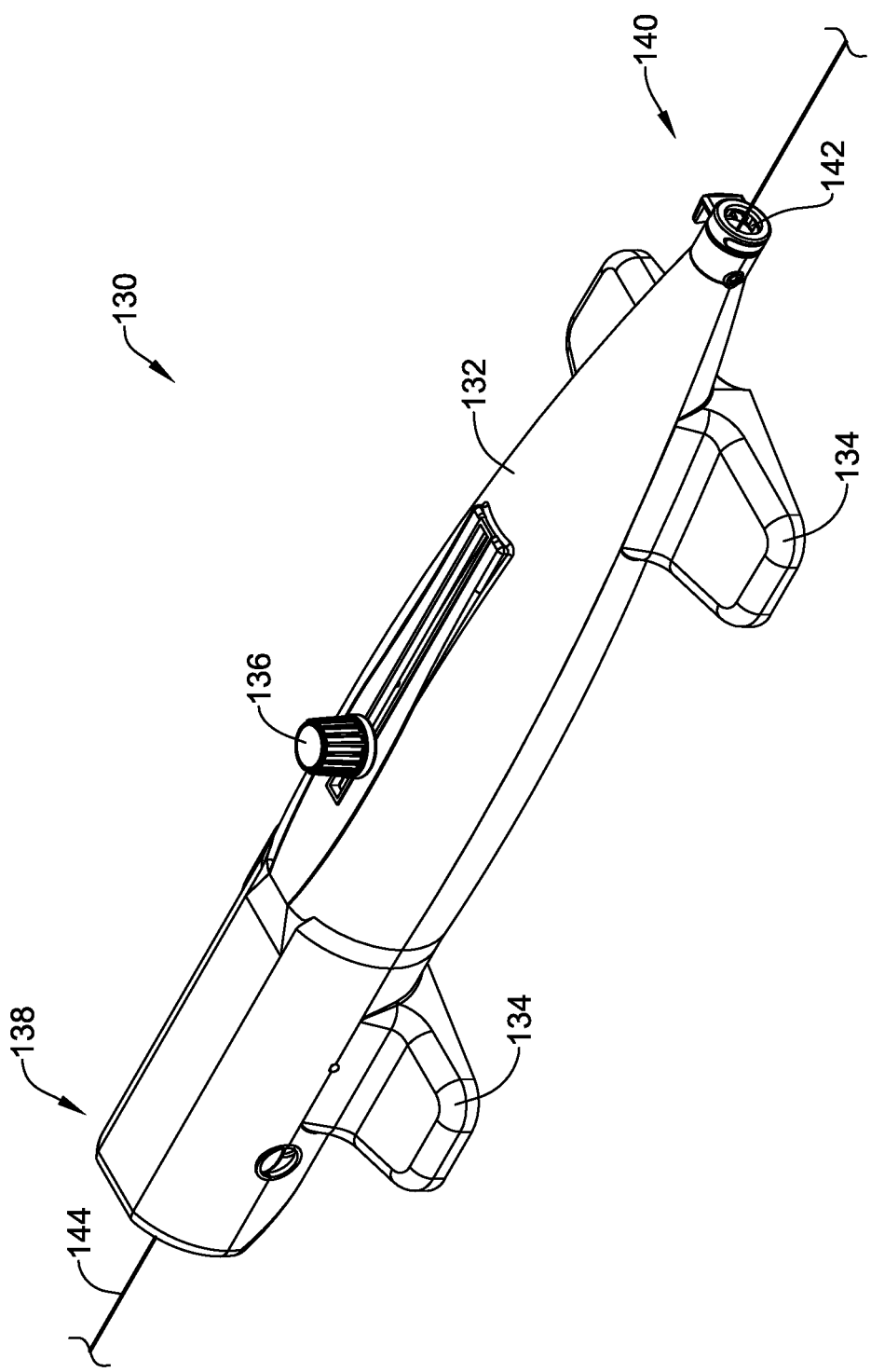
FIG. 7 is a perspective view of an example atherectomy system.

FIG. 7 is a perspective view of an example atherectomy system 130. In some cases, the atherectomy system 130 may be considered as being a manifestation of the atherectomy system 10, 20, 40, 50 or 90. In some instances, features of the atherectomy system 130 may be combined with features of any of the atherectomy systems 10, 20, 40, 50 or 90, for example. The atherectomy system 130 includes a handle 132. While not illustrated, it will be appreciated that the atherectomy system 132 includes a drive mechanism (such as the drive mechanism 12 shown in FIGS. 1-3) and a controller (such as the controller 16 shown in FIGS. 1-2) that is disposed within the handle 132 and that regulates operation of the drive mechanism. The handle 132 may, for example, include feet 134 that serve to stabilize the handle 132 on a flat surface during operation. A control mechanism 136 extends out of the handle 132 and may be used in controlling one or more features of the atherectomy system 132 during use. For example, the control mechanism 136 may be used to allow a user to change an operating speed of the drive mechanism.

The handle 132 includes a proximal region 138 and a distal region 140. As can be seen, the distal region 140 includes an aperture 142 that is adapted to permit a drive cable (such as the drive cable 24 of FIGS. 2 and 4) to exit the handle 132. While not visible, the proximal region 138 may be configured to accommodate a guidewire 144 extending through the atherectomy system 130. It will be appreciated that at the distal region 140, the guidewire 144 will extend through the drive cable that is not shown in this illustration. In some cases, the atherectomy burr 14 may be attached to a simple drive mechanism (not illustrated) that does not include the controls discussed herein.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An atherectomy system, comprising:
    an electric drive mechanism adapted to rotatably actuate an atherectomy burr; and
    a Proportional Integral Derivative (PID) controller adapted to regulate operation of the electric drive mechanism, the PID controller regulating operation of the electric drive mechanism in accordance with a power input limit value that limits how much power can be put into the atherectomy burr and an energy input limit value that limits how much energy can be put into the atherectomy burr.

2. The atherectomy system of claim 1, wherein the electric drive mechanism comprises:
    a drive cable adapted to be coupled with an atherectomy burr; and
    an electric drive motor that is adapted to rotate the drive cable.

3. The atherectomy system of claim 2, further comprising an atherectomy burr rotatably secured to the drive cable.

4. The atherectomy system of claim 1, wherein the PID controller is further adapted to regulate operation of the electric drive mechanism in accordance with a dynamic torque limit value.

5. The atherectomy system of claim 4, wherein the dynamic torque limit value varies in accordance with operating speed of the electric drive mechanism.

6. The atherectomy system of claim 1, wherein the PID controller is further adapted to provide feedback to an operator of the atherectomy system when either the power input limit value and/or the energy input limit value are exceed during operation of the atherectomy system.

7. The atherectomy system of claim 6, wherein the feedback comprises a temporary reduction in an operating speed of the electric drive mechanism.

8. The atherectomy system of claim 4, wherein the PID controller comprises:
    a speed reference block that includes the power input limit value and the energy input limit value and is configured to output a reference signal;
    a control block that is adapted to receive the reference signal from the speed reference block and generate a control effort signal; and a drive motor circuit block that is adapted to receive the control effort signal from the control block and regulate operation of the electric drive mechanism accordingly.

9. The atherectomy system of claim 8, wherein the drive motor circuit block includes the dynamic torque limit value and regulates operation of the electric drive mechanism accordingly.

10. The atherectomy system of claim 9, wherein the dynamic torque limit values comprises a current limit value.

11. An atherectomy system, comprising:
an electric drive motor operably coupled to a drive cable;
an atherectomy burr operably coupled to the drive cable; and
a control system operably coupled to the drive motor, the control system including:
a speed reference block that includes a power input limit value and an energy input limit value and is configured to output a reference signal;
a control block that is adapted to receive the reference signal from the speed reference block and generate a control effort signal;
a state estimation block that receives a position signal from the electric drive motor and outputs a motor speed signal that is summed with the reference signal from the speed reference block; and
a drive motor circuit block that is adapted to receive the control effort signal from the control block and regulate operation of the electric drive mechanism accordingly.

12. The atherectomy system of claim 11, wherein the electric drive motor comprises a brushless DC electric motor.

13. The atherectomy system of claim 11, wherein the drive motor circuit block further includes a dynamic torque limit value and regulates operation of the electric drive mechanism accordingly.

14. The atherectomy system of claim 13, wherein the dynamic torque limit values comprises a current limit value.

15. The atherectomy system of claim 11, wherein the control block comprises a Proportional Integral Derivative (PID) controller.

16. An atherectomy system, comprising:
an electric drive motor operably coupled to a drive cable;
an atherectomy burr operably coupled to the drive cable; and
a control system operably coupled to the drive motor, the control system including:
a speed reference block that includes a power input limit value and an energy input limit value and is configured to output a reference signal that is limited by at least one of the power input limit value and the energy input limit value;
a control block that is adapted to receive the reference signal from the speed reference block and generate a control effort signal;
a state estimation block that receives a position signal from the electric drive motor and outputs a motor speed signal that is summed with the reference signal from the speed reference block; and
a drive motor circuit block that is adapted to receive the control effort signal from the control block and includes a dynamic torque limit and regulates operation of the electric drive motor in accordance with the control effort signal and the dynamic torque limit.

17. The atherectomy system of claim 16, wherein the control system is further adapted to provide feedback to an operator of the atherectomy system when any of the power input limit value, the energy input limit value or the dynamic torque limit are approached or exceeded during operation of the atherectomy system.

18. The atherectomy system of claim 17, wherein the feedback comprises a discernible reduction in an operating speed of the electric drive mechanism.

* * * * *